(12) United States Patent
Lupotti

(10) Patent No.: US 11,179,193 B2
(45) Date of Patent: Nov. 23, 2021

(54) DEVICE FOR INTRAVASCULAR THERAPY AND/OR DIAGNOSIS

(71) Applicant: St. Jude Medical, Atrial Fibrillation Division, Inc., St. Paul, MN (US)

(72) Inventor: Fermin Armando Lupotti, Lake Forest, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 760 days.

(21) Appl. No.: 14/776,497

(22) PCT Filed: Mar. 14, 2014

(86) PCT No.: PCT/US2014/027234
§ 371 (c)(1),
(2) Date: Sep. 14, 2015

(87) PCT Pub. No.: WO2014/152344
PCT Pub. Date: Sep. 25, 2014

(65) Prior Publication Data
US 2016/0030108 A1    Feb. 4, 2016

Related U.S. Application Data

(60) Provisional application No. 61/790,533, filed on Mar. 15, 2013.

(51) Int. Cl.
*A61B 18/14*    (2006.01)
*A61B 8/12*    (2006.01)
(Continued)

(52) U.S. Cl.
CPC ........ *A61B 18/1492* (2013.01); *A61B 5/0066* (2013.01); *A61B 5/0084* (2013.01);
(Continued)

(58) Field of Classification Search
CPC ...... A61B 18/1492; A61B 2017/00057; A61B 2017/00106; A61B 2018/00267;
(Continued)

(56) References Cited

U.S. PATENT DOCUMENTS 5,409,000 A * 4/1995 Imran ............... A61B 8/12
600/374
5,752,518 A * 5/1998 McGee ............. A61B 8/12
600/424
(Continued)

FOREIGN PATENT DOCUMENTS

WO    2008049084 A2    5/1998
WO    1998018388 A1    7/1998
(Continued)

*Primary Examiner* — Yi-Shan Yang
(74) *Attorney, Agent, or Firm* — Dykema Gossett PLLC

(57) ABSTRACT

An elongate medical device may include an elongate body having a proximal end portion and a distal end portion and defining a longitudinal axis extending from the proximal end portion to the distal end portion. The elongate medical device may further include a basket assembly coupled to the distal end portion comprising a plurality of ablation elements, each of the ablation elements configured to ablate a respective target, the basket assembly disposed on a radial exterior of the elongate body. The elongate medical device may further include an imaging transmitter disposed radially-inward of the ablation elements and configured to project imaging energy towards at least one of the respective targets.

14 Claims, 4 Drawing Sheets

(51) Int. Cl.
*A61B 5/00* (2006.01)
*A61B 8/00* (2006.01)
*A61B 18/00* (2006.01)
*A61B 17/00* (2006.01)
*A61B 90/00* (2016.01)

(52) U.S. Cl.
CPC ............... *A61B 8/12* (2013.01); *A61B 8/445* (2013.01); *A61B 8/4416* (2013.01); *A61B 8/4494* (2013.01); *A61B 5/0095* (2013.01); *A61B 90/37* (2016.02); *A61B 2017/00057* (2013.01); *A61B 2017/00106* (2013.01); *A61B 2018/00267* (2013.01); *A61B 2018/00357* (2013.01); *A61B 2018/00404* (2013.01); *A61B 2018/00434* (2013.01); *A61B 2018/00511* (2013.01); *A61B 2018/00577* (2013.01); *A61B 2018/00982* (2013.01); *A61B 2090/3735* (2016.02); *A61B 2090/3782* (2016.02); *A61B 2090/3784* (2016.02); *A61B 2218/002* (2013.01)

(58) Field of Classification Search
CPC ........ A61B 2018/00577; A61B 5/0084; A61B 5/0095; A61B 8/12; A61B 8/445; A61B 8/4494; A61B 2090/3782; A61B 2090/3784; A61B 90/37
See application file for complete search history.

(56) References Cited

U.S. PATENT DOCUMENTS

| | | | |
|---|---|---|---|
| 6,092,528 A * | 7/2000 | Edwards | A61N 1/056 128/898 |
| 7,263,397 B2 | 8/2007 | Hauck et al. | |
| 7,648,462 B2 | 1/2010 | Jenkins et al. | |
| 7,885,707 B2 | 2/2011 | Hauck | |
| 8,588,885 B2 | 11/2013 | Hall et al. | |
| 8,825,130 B2 | 9/2014 | Just et al. | |
| 9,474,486 B2 | 10/2016 | Eliason et al. | |
| 2005/0096647 A1* | 5/2005 | Steinke | A61B 18/1492 606/41 |
| 2008/0039746 A1* | 2/2008 | Hissong | A61N 7/022 601/3 |
| 2008/0125772 A1* | 5/2008 | Stone | A61B 18/1492 606/41 |
| 2011/0257523 A1* | 10/2011 | Hastings | A61B 8/12 600/439 |
| 2012/0271170 A1* | 10/2012 | Emelianov | A61B 5/0095 600/439 |
| 2012/0302882 A1* | 11/2012 | Sliwa | A61B 8/12 600/439 |
| 2013/0066193 A1 | 3/2013 | Olson et al. | |
| 2013/0211292 A1* | 8/2013 | Sverdlik | A61B 17/2202 601/2 |
| 2015/0066014 A1* | 3/2015 | Sliwa | A61B 18/1492 606/34 |

FOREIGN PATENT DOCUMENTS

| | | |
|---|---|---|
| WO | 1999044520 A1 | 10/1999 |
| WO | 2013123014 A1 | 8/2013 |

\* cited by examiner

DEVICE FOR INTRAVASCULAR THERAPY AND/OR DIAGNOSIS

CROSS-REFERENCE TO RELATED APPLICATION

This application claims the benefit of U.S. provisional patent application No. 61/790,533, filed 15 Mar. 2013, which is hereby incorporated by reference in its entirety.

BACKGROUND a. Technical Field

The instant disclosure is directed to elongate medical devices, including elongate medical devices for ablation therapy and/or diagnosis of vasculature.

b. Background Art

A number of types of ablation procedures may be performed on the human vasculature. One such procedure is renal denervation. Through the application of a chemical agent, or a surgical procedure, or the application of energy, renal nerves may be removed or damaged to diminish renal nerve function. Renal denervation may result in a complete and permanent block of the renal nerves. Renal denervation diminishes or reduces renal sympathetic nerve activity, increases renal blood flow, and decreases renal plasma norepinephrine content. Another vasculature ablation procedure is pulmonary vein isolation. In pulmonary vein isolation, the pulmonary veins are ablated or otherwise damaged to help treat, for example, atrial fibrillation.

Renal denervation, pulmonary vein isolation, and other vasculature ablative techniques may involve the use of a catheter having a number of ablation elements on a basket structure on the distal end of the catheter. The ablation elements may be, for example, electrodes. Once inside the vessel to be ablated, the basket may be expanded to place the electrodes in contact with the vessel wall. Ablation energy may be delivered through the electrodes to ablate the vessel.

BRIEF SUMMARY

An elongate medical device including a basket assembly for ablation and imaging capability may be advantageous over known devices by providing direct visual feedback of the state of ablated tissue, which feedback is not provided by known ablation devices. An embodiment of such an elongate medical device may include an elongate body having a proximal end portion and a distal end portion and defining a longitudinal axis extending from the proximal end portion to the distal end portion. The elongate medical device may further include a basket assembly coupled to the distal end portion comprising a plurality of ablation elements, each of the ablation elements configured to ablate a respective target, the basket assembly disposed on a radial exterior of the elongate body. The elongate medical device may further include an imaging transmitter disposed radially-inward of the ablation elements and configured to project imaging energy towards at least one of the respective targets.

Another embodiment of an elongate medical device that improves on known devices as described above may comprise an elongate body having a proximal end portion and a distal end portion and defining a longitudinal axis extending from the proximal end portion to the distal end portion. The elongate medical device may also include a basket assembly coupled to the distal end portion comprising a plurality of ablation elements, each of the ablation elements configured to ablate a respective target, the basket assembly disposed on a radial exterior of the elongate body. The elongate medical device may further include a first imaging transmitter comprising an ultrasound transducer, the first imaging transmitter disposed radially-inward of the ablation elements and configured to project first imaging energy towards at least one of the respective targets and a second imaging transmitter disposed radially-inward of said ablation elements and configured to project second imaging energy towards the one target.

A system that improves on systems including known devices as described above may include an elongate medical device and a movement mechanism. The elongate medical device may comprise an elongate body having a proximal end portion and a distal end portion and defining a longitudinal axis extending from the proximal end portion to the distal end portion. The elongate medical device may further include a basket assembly coupled to the distal end portion comprising a plurality of ablation elements, each of the ablation elements configured to ablate a respective target, the basket assembly disposed on a radial exterior of the elongate body. The elongate medical device may further include an imaging transmitter disposed radially-inward of the ablation elements, configured to project imaging energy, and configured to move relative to the ablation elements so as to selectively project imaging energy towards each of the targets. The movement mechanism may be disposed outside of the elongate body, may be mechanically coupled with the imaging transmitter, and may be configured to move the imaging transmitter relative to the ablation elements.

DETAILED DESCRIPTION OF THE DRAWINGS

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
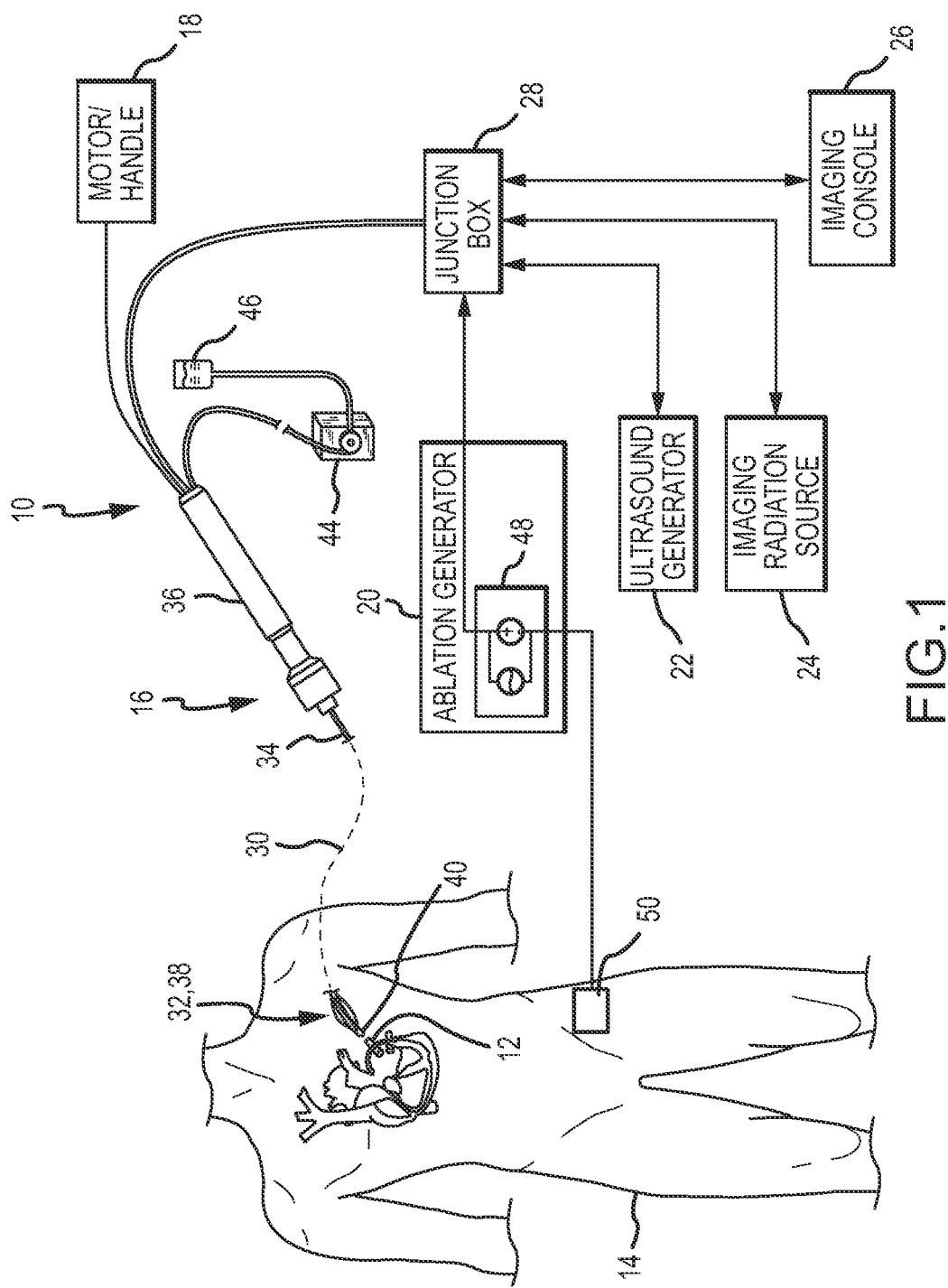
FIG. 1 is diagrammatic view of an ablation system.

Referring to the drawings, in which like numerals refer to the same or similar elements in the various views, FIG. 1 is a diagrammatic view of a system 10 for performing an ablation procedure on a tissue 12 of a patient's body 14. The tissue 12 may be, for example and without limitation, a pulmonary vein, a renal artery, another portion of the patient's vasculature, or other tissue. The system 10 may include an elongate medical device 16, an exterior motor/handle 18, an ablation generator 20, an ultrasound generator 22, an imaging radiation source 24, an imaging console 26, and a junction box 28.

The elongate medical device 16 may be, in an embodiment, a catheter (i.e., catheter 16). In other embodiments, the elongate medical device 16 may instead be an introducer or another known medical device type. The following discussion will be with respect to an embodiment in which the elongate medical device 16 is a catheter, but it should be understood that the elongate medical device 16 is not limited to any particular type of medical device.

The catheter 16 may include an elongate, flexible body or shaft 30, the shaft 30 having a distal end portion 32 and a proximal end portion 34, and a handle 36 coupled to the proximal end portion 34. The distal end portion 32 may include or be coupled to a basket assembly 38 and a tip electrode 40. In addition to the tip electrode 40, the distal end portion 32 may include one or more ablation elements 42 (see FIG. 2A) that may be used, for example and without limitation, for the application of ablation energy or chemicals. The tip electrode 40 may also be used for the application of ablation energy. The ablation elements 42 may be disposed on the basket assembly 38, as shown in FIGS. 2A-4B, or otherwise disposed on the shaft 30. In an embodiment, the ablation elements 42 may be electrodes. In other embodiments, the ablation elements 42 may be cryo probes, ultrasound transducers, or other known devices for applying ablation energy or chemicals. The following discussion will be with respect to an embodiment in which the ablation elements 42 are electrodes (i.e., electrodes 42), but it should be understood that neither the catheter 16 nor the system 10 is not limited to electrode-based ablation.

With continued reference to FIG. 1, the electrodes 42 may also be used, in an embodiment, for positioning, for mapping of anatomical structures, and for the collection of electrophysiology data and other electrical data respective of patient tissue. In embodiments, other sensors (not shown) may additionally or alternatively be provided in or on the catheter 16 for such positioning, mapping, and/or data collection. Accordingly, the catheter 16 may be connected to a mapping and navigation system (not shown), in embodiments. Exemplary mapping and navigation systems are shown and described in U.S. patent application Ser. Nos. 13/231,284; 10/819,027 (issued as U.S. Pat. No. 7,263,397); and Ser. No. 11/227,580 (issued as U.S. Pat. No. 7,885,707), each of which is hereby incorporated by reference in its entirety as though fully set forth herein.

The distal end portion 32 of the shaft 30 may also include one or more imaging transmitters and/or receivers (shown in FIGS. 2A and 3-4B). Such imaging transmitters and/or receivers may include or comprise one or more ultrasound transducers, one or more optical transmitters and/or receivers (e.g., implemented via optical fibers), and/or other known imaging devices.

For irrigation and other known purposes, the catheter 16 may be coupled to a source or destination of fluids, in an embodiment, such as a pump 44 which may comprise, for example, a fixed or variable rate roller pump or variable volume syringe pump with a gravity feed supply from a fluid source 46.

The ablation generator 20 may be provided as a source of ablation energy for the electrodes 40, 42. The ablation generator 20 may generate, deliver, and control RF energy output by the catheter 16, and the electrodes 40, 42, in particular. The generator 20 may be conventional in the art and may comprise a commercially available unit, such as that sold under the model number IBI-1500T-11 RF cardiac ablation generator, available from St. Jude Medical, Inc. The ablation generator 20 may include an RF ablation signal source 48 configured to generate an ablation signal driven between one or more electrodes 40, 42 on the catheter 16 and an RF indifferent/dispersive patch 50 placed on the patient's skin. In embodiments in which the system 10 is configured for ablation through means other than RF (e.g., ultrasound ablation, cryoablation), the system may include additional or alternative components known in the art for performing the ablation procedure.

The ultrasound generator 22 may be provided as a source of ultrasound energy for one or more ultrasound transducers in the distal end portion 32 of the shaft 30 (see FIGS. 2A-4B). The ultrasound generator 22 may be conventional in the art and may be operated independently or under the control of the imaging console 26 or of another system or device, in embodiments.

Figure 4A:
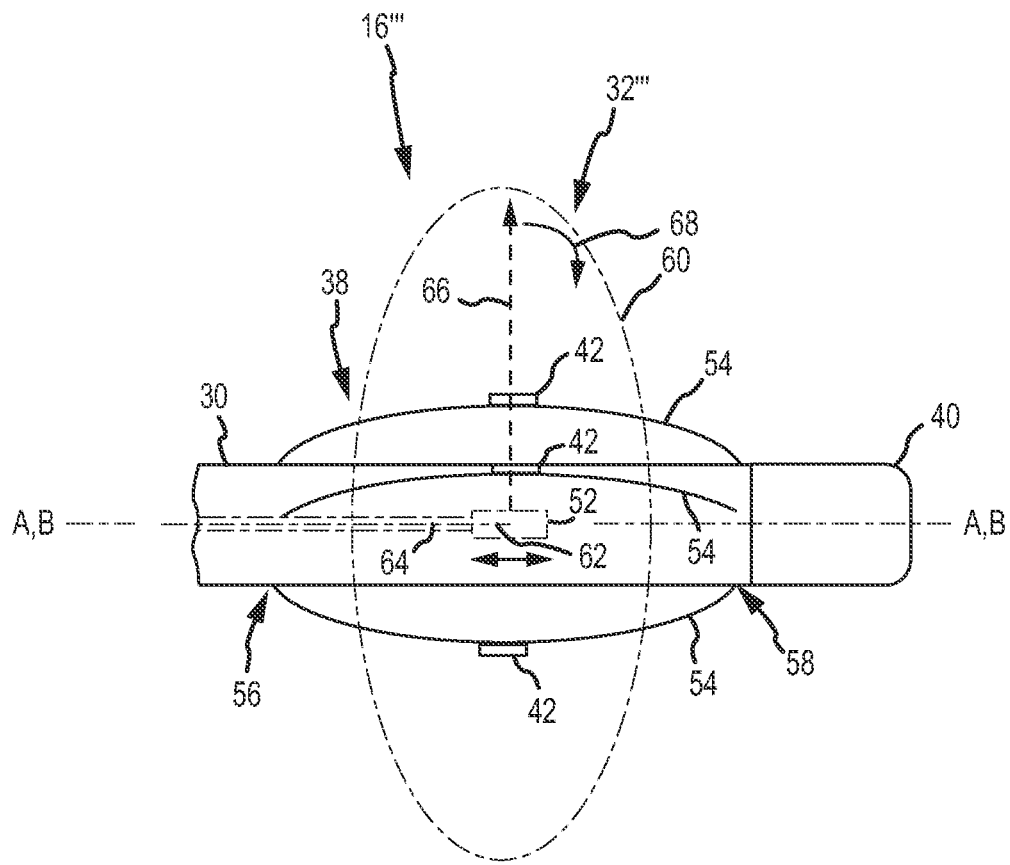
FIG. 4A is a diagrammatic side view of a portion of an embodiment of an elongate medical device that may be used in the system of FIG. 1.
Figure 4B:
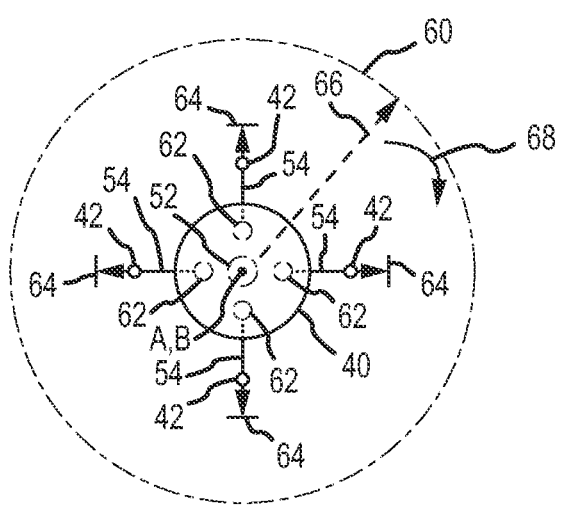
FIG. 4B is a diagrammatic distal end view of the elongate medical device portion of FIG. 4A.

The imaging radiation source 24 may be provided as a source of imaging radiation for one or more imaging transmitters in the distal end portion 32 of the shaft 30 (see FIGS. 4A and 4B). In an embodiment, the imaging radiation source 24 may be configured to provide imaging radiation having selected characteristics, such as frequency, power, etc. The imaging radiation source 24 may allow the characteristics of the imaging radiation to be altered by a user or control device, either before or during a medical procedure (e.g., an ablation procedure). In an embodiment, the imaging radiation source may provide imaging radiation for photoacoustic imaging and/or optical coherence tomography (OCT). The imaging radiation source 24 may thus be coupled with one or more optical fibers extending through the catheter 16 (see FIGS. 4A and 4B) or otherwise with one or more optical transmitters or other imaging transmitters. The imaging radiation source may be operated independently or under the control of the imaging console 26 or of another system or device, in embodiments.

The imaging console 26 may be provided to generate and display images based on applied radiation from the ultrasound generator 22 and/or imaging radiation source 24. Accordingly, the imaging console 26 may be provided with image processing capabilities to construct ultrasound and/or photoacoustic images based on echoes received by an ultrasound transducer within the catheter 16, optical images based on signals generated by an optical receiver within the catheter 16, and other images, as known in the art. An exemplary system for generating photoacoustic images, portions of which system may be incorporated into the system 10, is shown and described in greater detail in International (PCT) Patent Application No. PCT/US13/25890, which is hereby incorporated by reference in its entirety as though fully set forth herein. The imaging console 26 may also provide an interface through which a user may control the ultrasound generator 22 and/or the imaging radiation source 24, in embodiments.

The junction box 28 may provide an electrical connection interface for the catheter 16, ablation generator 20, ultrasound generator 22, imaging radiation source 24, and imaging console 26. Accordingly, the junction box 28 may include a plurality of connectors or sockets for the various components of the system 10. The junction box 28 may include various transformers, electromagnetic isolation circuitry, and other circuitry as known in the art. One example of an isolation box, the concepts and components of which may be incorporated into the junction box 28, is shown and described in U.S. Pat. No. 7,648,462, which is hereby incorporated by reference in its entirety as though fully set forth herein.

The motor/handle 18 may be provided as a mechanism to direct movement of one or more elements within the catheter. The motor/handle may be partially or entirely disposed outside of the catheter 16, in an embodiment. The motor/handle 18 may be mechanically coupled with an ultrasound transducer and/or one or more other imaging transmitters within the catheter shaft for longitudinal and/or rotational movement. As used herein, longitudinal movement refers to translational movement along a longitudinal axis, such as the longitudinal axis of the shaft 30, and rotational movement refers to rotation around the axis of the shaft 30 or around an axis that is substantially parallel to the axis of the shaft 30. The motor/handle 18 may include a motor, which may itself be configured for manual control by a physician and/or for automated movement. The motor/handle 18 may additionally or alternatively include a handle for manual direction of movement by the physician. In an embodiment, such a handle may be incorporated directly into the catheter handle 36.

Figure 2A:
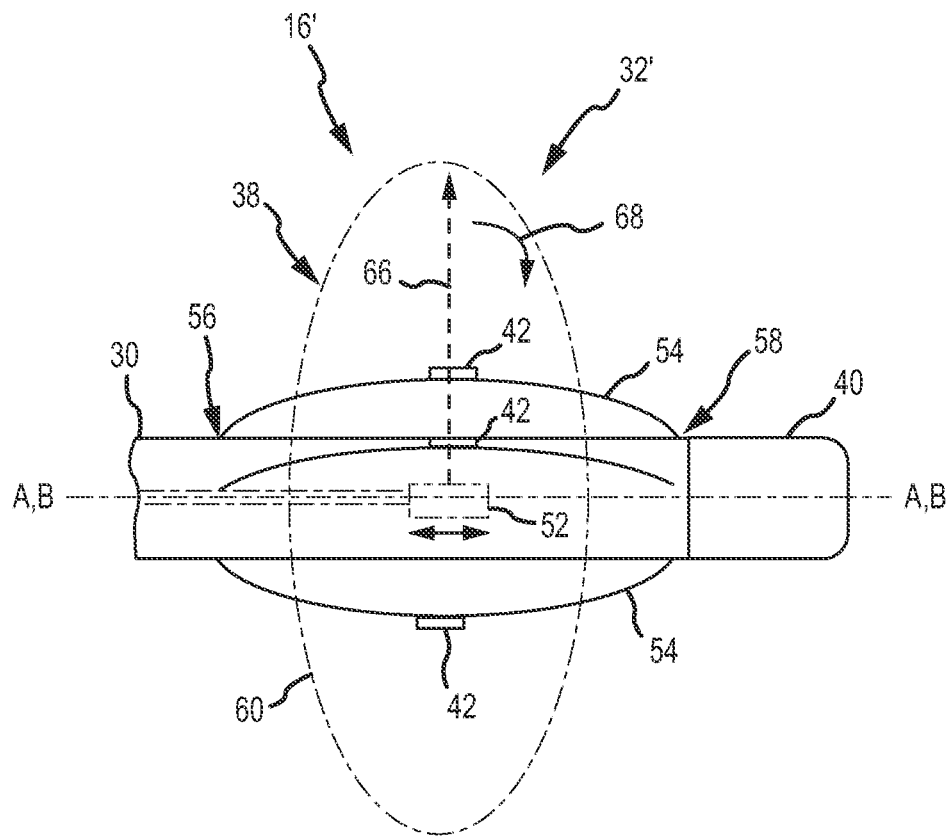
FIG. 2A is a diagrammatic side view of a portion of an embodiment of an elongate medical device that may be used in the system of FIG. 1.
Figure 2B:
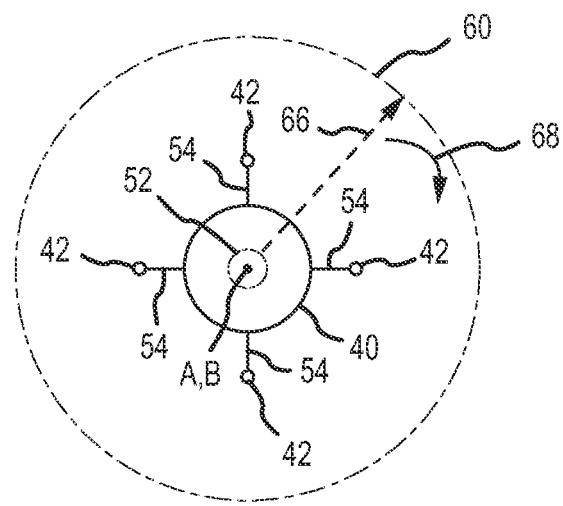
FIG. 2B is a diagrammatic distal end view of the elongate medical device portion of FIG. 2A.

FIG. 2A is a diagrammatic side view of a distal end portion 32' of an embodiment of the catheter 16', and FIG. 2B is a diagrammatic distal end view of the distal end portion 32'. Referring to FIGS. 2A and 2B, the distal end portion 32' may include a tip electrode 40, an ultrasound transducer 52 disposed within the shaft 30, and may further include or be coupled with a basket assembly 38. The shaft 30 may define a longitudinal axis A that extends from the distal end portion 32' to a proximal end portion (i.e., that is the same as or substantially similar to the proximal end portion 34 shown in FIG. 1) and around which the shaft 30 is radially symmetric. The basket assembly 38 may be disposed on the radial exterior of the distal end portion 32'. The basket assembly 38 may be expandable—i.e., may be configured to assume a compressed state as the distal end portion 32' is maneuvered through an introducer sheath (not shown) to a region of interest in the patient body and an expanded state once the distal end portion 32' reaches the region of interest and emerges from the sheath. The basket assembly 38 may include a plurality of splines 54 on which a plurality of electrodes 42 are disposed. The splines 54 may be coupled together or to common portions of the shaft 30 at a proximal end 56 and at a distal end 58 of the basket assembly 38 and may bow outward (i.e., assume a bowed shape) when the basket assembly is in the expanded state. In an embodiment, the basket assembly may comprise a helical configuration or assembly similar to that described in or according to the teachings of U.S. patent application Ser. Nos. 13/790,110; 13/072,357 (published as United States patent application publication no. US 2011/0213231 A1); and Ser. No. 13/340,760, each of which is hereby incorporated by reference in its entirety as though fully set forth herein.

In an embodiment, the basket assembly 38 may comprise four (4) splines 54 and four (4) electrodes 42, with one electrode 42 on each spline 54. Of course, in various embodiments, any number of splines 54 may be used, any number of electrodes 42 may be placed on respective splines 54, and different splines 54 may have the same number or different numbers of electrodes 42. The electrodes 42 may be disposed at the same or substantially the same longitudinal position on respective splines 54 (i.e., when the splines 54 are in an expanded state), in an embodiment. The electrodes 42 may comprise metal, or may comprise a material that is transparent or semi-transparent to some types of imaging radiation, such as ultrasound, as known in the art.

The ultrasound transducer 52 may be movably disposed within the catheter shaft 30 or otherwise radially-inward of the basket assembly 38 and of the electrodes 42 on the basket assembly 38. The ultrasound transducer 52 may define a transducer axis B that, as shown in FIG. 2A, may be substantially coincident with catheter axis A. In embodiments, the transducer axis B may be radially offset from the catheter axis A, but substantially parallel with the catheter axis A. In an embodiment, the ultrasound transducer 52 may be configured for both longitudinal and rotational movement relative to the shaft 30, relative to the basket assembly 38, and relative to the electrodes 42. The ultrasound transducer 52 may be coupled to a movement mechanism that may allow manipulation of the longitudinal and/or rotational position of the ultrasound transducer (e.g., motor/handle 18 in FIG. 1). The movement mechanism may allow for manual manipulation of the ultrasound transducer's position and orientation and/or for motorized and/or automated movement of the ultrasound transducer 52. The ultrasound transducer 52 may be configured, under either manual or motorized or otherwise automated movement, to be stopped from rotating to focus on a particular location or to create a single line (M-mode-like) trace.

With continued reference to FIGS. 2A and 2B, the ultrasound transducer 52 may operate as an imaging transmitter and/or receiver, and thus may be configured to project ultrasound energy and to receive the resultant echoes. In an embodiment, the ultrasound transducer 52 may also be configured to receive ultrasound energy generated by the application of optical energy or other imaging energy to tissue (i.e., to generate a photoacoustic image). In an embodiment, the ultrasound transducer 52 may be configured to project ultrasound energy radially—i.e., to image an area that is at the same longitudinal position along the catheter axis A as is the ultrasound transducer 52. In embodiments in which the ultrasound transducer 52 is configured to rotate about the transducer axis B, the transducer 52 may have an imaging plane 60 that is transverse to the catheter shaft 30, transverse to the vessel in which the distal end portion 32' is disposed, and at the same longitudinal position as the ultrasound transducer 52. The transducer 52 may project ultrasound along an imaging axis 66, which may rotate in a direction 68 to form imaging plane 60. By placing the ultrasound transducer 52 at the same longitudinal position as one or more of the electrodes 42, the ultrasound transducer 52 may be used to view an imaging plane 60 that includes tissue being ablated by the electrodes 42.

In an embodiment, instead of or in addition to a single, rotatable ultrasound transducer 52, the catheter may include a one or more rotationally-fixed ultrasound transducers. Each of the rotationally-fixed ultrasound transducers may be configured to project ultrasound energy at a respective ablation target (i.e., tissue being ablated by a respective electrode 42).

The ultrasound transducer 52 provides an advantage over known devices for vascular ablation, especially known basket catheters. Known basket ablation catheters generally do not provide any direct feedback to the physician that allow the physician to determine if the ablation procedure has been completed—any feedback must come from additional devices. The ultrasound transducer 52 in the distal end portion 32' allows a physician using the catheter 16' to observe ablated tissue before, during, and after ablation to confirm that the ablation procedure has caused the appropriate and desired physiological changes.

Figure 3:
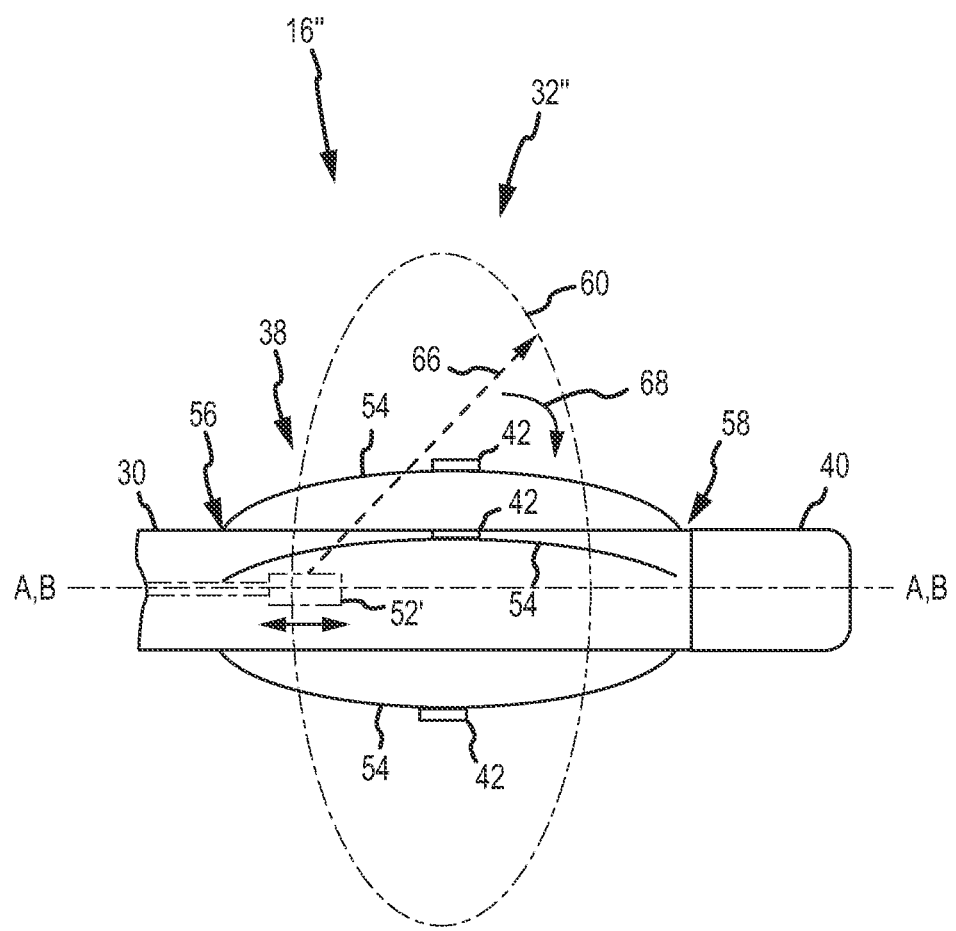
FIG. 3 is a diagrammatic side view of a portion of an embodiment of an elongate medical device that may be used in the system of FIG. 1.

FIG. 3 is a diagrammatic side view of the distal end portion 32" of another embodiment of the catheter 16". The catheter 16" shown in FIG. 3 is the same as the catheter 16' shown in FIGS. 2A and 2B, except the catheter 16" shown in FIG. 3 has a "forward-looking" ultrasound transducer 52'. Accordingly, the "forward-looking" ultrasound transducer 52' may be placed longitudinally proximal of the electrodes 42 to image the tissue being ablated by the electrodes 42. The ultrasound transducer 52' may be configured to rotate about the transducer axis B, and may have an imaging plane 60 that is transverse to the distal end portion 32" and to the vessel in which the distal end portion 32" is disposed. As noted above, one or more rotationally-fixed transducers may be used instead of or in addition to the rotatable ultrasound transducer 52'. The catheter 16" illustrated in FIG. 3 may be preferred over the catheter 16' illustrated in FIGS. 2A and 2B in embodiments in which the electrodes 42 are opaque or semi-opaque to ultrasound, as the forward-looking transducer 52' looks "around" an electrode 42 instead of "through" an electrode 42. Furthermore, the transducer 52' may be configured to be "backward-looking," in an embodiment, in addition to or instead of being forward-looking. Still further, the transducer 52' may comprise a mirror element (e.g., under motorized or manual control as described herein) that may be used to adjust the angle at which ultrasound energy projects from the transducer 52'.

FIG. 4A is a diagrammatic side view of the distal end portion 32''' of another embodiment of the catheter 16''', and FIG. 4B is a diagrammatic distal end view of the distal end portion 32'''. The catheter 16''' shown in FIGS. 4A and 4B is the same as the catheter 16' shown in FIGS. 2A and 2B, but the catheter 16''' additionally includes a plurality of imaging transmitters. The imaging transmitters may be optical transmitters, in an embodiment, disposed at the end of respective optical fibers 64. The catheter 16''' will be discussed with reference to an embodiment in which each of the imaging transmitters is an optical transmitter (i.e., optical transmitter 62), but it should be understood that the imaging transmitters are not so limited.

In an embodiment, the catheter 16' may include an equal number of optical transmitters 62 as electrodes 42 and/or splines 54 on the basket assembly 38. In the embodiment shown in FIGS. 4A and 4B, the catheter 16' includes four (4) splines 54, four (4) electrodes 42, and four (4) optical transmitters 62. Each of the optical transmitters 62 may be configured to project imaging radiation at a respective field of view 64, which field of view 64 may coincide with a respective ablation target, i.e., the tissue or tissue portion ablated by a respective electrode 42 (or, in embodiments, by multiple electrodes 42).

The optical transmitters 62 may also operate as optical receivers (i.e., in a time-multiplexed fashion, in an embodiment). Additionally or alternatively, the optical transmitters 62 may be paired with respective optical receivers (not shown), in an embodiment. Each of the optical transmitters 62 may thus be configured to project optical energy into tissue (e.g., tissue ablated by an electrode 42). The optical transmitters 62 (or paired optical receivers) may be further configured to receive optical energy reflected back from the tissue and to transmit signals based on received optical energy to form an OCT image.

The imaging radiation projected by the optical transmitters 62 may be used, for example only and without limitation, for photoacoustic imaging (e.g., in conjunction with the ultrasound transducer 52) and/or OCT. In an exemplary renal denervation procedure, a physician may ablate a renal artery with the electrodes 40, 42 while observing the ablated area via an ultrasound image produced according to echoes received by the ultrasound transducer 52. During or after the procedure, the physician may additionally view an OCT image and/or a photoacoustic image to observe the ablated tissue at different depths and/or resolutions. By using multiple imaging modalities, the physician may more accurately determine if an ablation procedure has produced the desired physiological changes.

Although a number of embodiments have been described above with a certain degree of particularity, those skilled in the art could make numerous alterations to the disclosed embodiments without departing from the spirit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of this disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An elongate medical device comprising:
   an elongate body having a proximal end portion and a distal end portion and defining a lumen and a longitudinal axis extending through the elongate body, from said proximal end portion to said distal end portion;
   a basket assembly having a distal basket end and a proximal basket end,
      wherein the elongate body extends through the proximal basket end to the distal basket end, extends through the distal basket end, and is connected to the distal basket end, the basket assembly comprising a plurality of ablation elements, each of said plurality of ablation elements configured to ablate a respective target, said basket assembly disposed on a radial exterior of said elongate body; and
   an imaging transmitter disposed within the lumen, radially-inward of said plurality of ablation elements and configured to project imaging energy towards at least one of said respective targets via a mirror element,
      wherein the mirror element is configured to adjust an angle at which the imaging energy is projected from the imaging transmitter,
      wherein the angle is adjustable, and
      wherein the imaging transmitter is configured to translate axially through the lumen of the elongate body from the proximal basket end to the distal basket end.

2. The elongate medical device of claim 1, wherein said imaging transmitter comprises an ultrasound transducer.

3. The elongate medical device of claim 1, wherein said imaging transmitter is configured to translate axially along the longitudinal axis relative to one or more of said plurality of ablation elements.

4. The elongate medical device of claim 1, wherein said imaging transmitter is configured to rotate, relative to one or more of said plurality of ablation elements, around a transmitter axis that is substantially parallel to said longitudinal axis.

5. The elongate medical device of claim 1, wherein at least two of said plurality of ablation elements are disposed at a substantially same longitudinal position on said basket assembly.

6. The elongate medical device of claim 5, wherein at least four of said plurality of ablation elements are disposed at substantially the same longitudinal position on said basket assembly.

7. The elongate medical device of claim 1, wherein said imaging transmitter comprises a plurality of imaging transmitters, each of said imaging transmitters configured to project the imaging energy towards a separate one of a plurality of tissue portions.

8. The elongate medical device of claim 1, wherein the imaging energy is directed toward the distal end portion.

9. The elongate medical device of claim 1, wherein the imaging transmitter directs the imaging energy to tissue adjacent to an outwardly facing side of the ablation element.

10. The elongate medical device of claim 9, wherein the imaging transmitter directs the imaging energy around the ablation element.

11. A system comprising:
    an elongate medical device comprising:
       an elongate body having a proximal end portion and a distal end portion and defining a lumen and a longitudinal axis extending from said proximal end portion to said distal end portion;
       a basket assembly having a distal basket end and a proximal basket end, wherein the elongate body extends through the proximal basket end to the distal basket end, through the distal basket end, and is connected to the distal basket end, the basket assembly comprising a plurality of ablation elements, each of said plurality of ablation elements configured to ablate a respective target, said basket assembly disposed on a radial exterior of said elongate body;
       an imaging transmitter disposed within the lumen, radially-inward of said plurality of ablation elements, configured to project imaging energy via a mirror element, and configured to move relative to said plurality of ablation elements so as to selectively project imaging energy towards each of said targets by moving with respect to each one of the ablation elements,
          wherein the mirror element is configured to adjust an angle at which the imaging energy is projected from the imaging transmitter,
          wherein the angle is adjustable,
          wherein the imaging transmitter is configured to translate axially through the lumen of the elongate body from the proximal basket end to the distal basket end; and
       a movement mechanism, disposed outside of said elongate body and mechanically coupled with said imaging transmitter, configured to move said imaging transmitter relative to said plurality of ablation elements.

12. The system of claim 11, wherein said movement mechanism comprises a motor.

13. The system of claim 11, wherein said movement mechanism is configured for manual movement of said imaging transmitter.

14. The system of claim 11, wherein the imaging energy is directed toward the proximal end portion.

* * * * *